(12) United States Patent
Mamedov et al.

(10) Patent No.: US 8,921,631 B2
(45) Date of Patent: Dec. 30, 2014

(54) SELECTIVE CATALYTIC HYDROGENATION OF ALKYNES TO CORRESPONDING ALKENES

(75) Inventors: Aggadin Kh. Mamedov, Sugar Land, TX (US); Saeed Mohammed Al-Wahabi, Riyadh (SA)

(73) Assignee: Saudi Basic Industries Corporation, Riyadh (SA)

( * ) Notice: Subject to any disclaimer, the term of this patent is extended or adjusted under 35 U.S.C. 154(b) by 494 days.

(21) Appl. No.: 13/140,881

(22) PCT Filed: Dec. 15, 2009

(86) PCT No.: PCT/EP2009/008962
§ 371 (c)(1),
(2), (4) Date: Sep. 12, 2011

(87) PCT Pub. No.: WO2010/069543
PCT Pub. Date: Jun. 24, 2010

(65) Prior Publication Data
US 2011/0313220 A1   Dec. 22, 2011

(30) Foreign Application Priority Data
Dec. 18, 2008   (EP) .................................... 08021964

(51) Int. Cl.
| | | |
|---|---|---|
| *C07C 5/05* | (2006.01) | |
| *C07C 7/167* | (2006.01) | |
| *B01J 21/02* | (2006.01) | |
| *B01J 21/06* | (2006.01) | |
| *B01J 23/00* | (2006.01) | |
| *B01J 23/40* | (2006.01) | |
| *B01J 23/755* | (2006.01) | |
| *B01J 23/652* | (2006.01) | |
| *B01J 23/86* | (2006.01) | |
| *B01J 23/89* | (2006.01) | |
| *B01J 35/00* | (2006.01) | |
| *B01J 37/02* | (2006.01) | |

(52) U.S. Cl.
CPC .................. *C07C 7/167* (2013.01); *B01J 21/02* (2013.01); *B01J 21/06* (2013.01); *B01J 21/063* (2013.01); *B01J 23/002* (2013.01); *B01J 23/40* (2013.01); *B01J 23/755* (2013.01); *B01J 23/652* (2013.01); *B01J 23/86* (2013.01); *B01J 23/89* (2013.01); *B01J 23/8946* (2013.01); *B01J 35/0006* (2013.01); *B01J 37/0201* (2013.01); *B01J 2523/00* (2013.01); *C07C 2521/02* (2013.01); *C07C 2523/44* (2013.01)
USPC ........... 585/274; 585/271; 585/250; 585/258; 585/259; 585/260; 502/207; 502/204; 502/202

(58) Field of Classification Search
USPC ......... 585/274, 259, 260, 261, 262, 258, 250, 585/271; 502/207, 204, 202
See application file for complete search history.

(56) References Cited

U.S. PATENT DOCUMENTS

| | | | |
|---|---|---|---|
| 3,821,323 A | 6/1974 | Schulze et al. | |
| 3,883,442 A | 5/1975 | McArthur | |
| 3,912,789 A | 10/1975 | Frevel et al. | |
| 4,024,171 A * | 5/1977 | McArthur | ..................... 518/715 |
| 4,034,061 A | 7/1977 | McArthur | |
| 4,112,007 A | 9/1978 | Sanfilippo et al. | |
| 4,227,025 A | 10/1980 | Montgomery | |
| 4,400,124 A | 8/1983 | Greller | |
| 4,404,124 A | 9/1983 | Johnson et al. | |
| 4,490,481 A | 12/1984 | Boitiaux et al. | |
| 4,906,800 A | 3/1990 | Henry et al. | |
| 5,356,851 A | 10/1994 | Sarrazin et al. | |
| 5,364,998 A | 11/1994 | Sarrazin et al. | |
| 5,463,154 A | 10/1995 | Slim et al. | |
| 5,587,348 A | 12/1996 | Brown et al. | |
| 5,648,576 A | 7/1997 | Nguyen Than et al. | |
| 5,705,723 A | 1/1998 | Kallenbach et al. | |
| 5,750,806 A | 5/1998 | Brocker et al. | |
| 5,866,735 A | 2/1999 | Cheung et al. | |
| 5,955,397 A | 9/1999 | Didillon et al. | |
| 5,994,257 A | 11/1999 | Kallenbach | |
| 6,037,301 A * | 3/2000 | Min et al. | ....................... 502/207 |
| 6,350,717 B1 | 2/2002 | Frenzel et al. | |
| 6,459,008 B1 | 10/2002 | Dai et al. | |
| 6,465,391 B1 * | 10/2002 | Cheung et al. | ................. 502/330 |
| 6,822,127 B2 | 11/2004 | Dai et al. | |
| 7,038,097 B2 | 5/2006 | Molinier et al. | |

(Continued)

FOREIGN PATENT DOCUMENTS

| | | |
|---|---|---|
| CN | 1640541 A1 | 7/2005 |
| EP | 0689872 B1 | 8/2001 |

(Continued)

OTHER PUBLICATIONS

Extended European Search Report; European Application No. 08021964.5; Date of Mailing: May 14, 2009; 8 Pages.
International Search Report; International Application No. PCT/EP2009/008962; International Filing Date: Dec. 15, 2009; Date of Mailing: Mar. 30, 2010; 7 Pages.
Written Opinion of the International Searching Authority; International Application No. PCT/EP2009/008962; International Filing Date: Dec. 15, 2009; Date of Mailing: Mar. 30, 2010; 8 Pages.

(Continued)

*Primary Examiner* — In Suk Bullock
*Assistant Examiner* — Sharon Pregler
(74) *Attorney, Agent, or Firm* — Cantor Colburn LLP

(57) ABSTRACT

The invention relates to a process for selectively hydrogenating an alkyne to the corresponding alkene comprising a step of contacting a gaseous feed comprising hydrogen and 0.1 to 20 mass % of alkyne with a catalyst comprising at least one Group 10 element on a boron-modified support. The process shows high conversion and good selectivity, and can be stably operated also if the feed comprises more than 2 mass % of alkyne.

11 Claims, No Drawings

(56) References Cited

U.S. PATENT DOCUMENTS

| | | |
|---|---|---|
| 7,153,807 B2 | 12/2006 | Molinier et al. |
| 2004/0192983 A1 | 9/2004 | Bergmeister et al. |
| 2006/0229478 A1 | 10/2006 | Moon et al. |

FOREIGN PATENT DOCUMENTS

| | | |
|---|---|---|
| EP | 1110606 B1 | 5/2005 |
| GB | 871804 | 2/1957 |
| WO | 9943429 A1 | 9/1999 |
| WO | 0216032 A1 | 2/2002 |
| WO | 03106020 A1 | 12/2003 |
| WO | 2006105799 A2 | 10/2006 |

OTHER PUBLICATIONS

Chinese Patent No. 164054; Date of Publication; Jul. 20, 2005; Abstract Only, 2 pages.

* cited by examiner

SELECTIVE CATALYTIC HYDROGENATION OF ALKYNES TO CORRESPONDING ALKENES

CROSS REFERENCE TO RELATED APPLICATIONS

This application is a 371 of International Application No. PCT/EP2009/008962, filed Dec. 15, 2009, which claims priority to European Application No. 08021964.5.5, filed Dec. 18, 2008, both of which are hereby incorporated by reference in its entirety.

TECHNICAL FIELD

The invention relates to a process for selective hydrogenation of an alkyne to the corresponding alkene comprising a step of contacting a gaseous feed comprising hydrogen and alkyne with a supported Group 10 metal catalyst.

BACKGROUND

Such a process is known from WO2006/105799. This document discloses a method for selective hydrogenation of acetylene to ethylene wherein a feed comprising acetylene and hydrogen is contacted with a $TiO_2$ supported Group 10 metal catalyst in a fixed bed reactor, and wherein the catalyst is diluted with a inert solid like $SiO_2$, $ZrO_2$, $Al_2O_3$ or $TiO_2$, preferably at a weight ratio of diluent to supported catalyst of from about 50 to about 170. The catalyst is reported to be suitable for converting acetylene in a gas stream that contains up to 20 mass % of acetylene.

Selective hydrogenation of alkynes to the corresponding alkenes is industrially important. Numerous documents focus on processes to remove acetylenic impurities, typically present in concentrations of 0.5-1 mol %, from ethylene.

Ethylene is a major intermediate for various chemicals, for example as a monomer that is used for the preparation of a large number of polymers. Ethylene is generally obtained by a hydrocarbon pyrolysis or steam cracking process, followed by separation steps. Polymer grade ethylene needs to be of high purity, and maximum allowable acetylene level is about 10 or even 5 ppm. One of the techniques used to free ethylene from any acetylene impurities is to selectively hydrogenate acetylene to ethylene over a palladium based catalyst supported on a suitable support such as alumina. A general problem with such metal based catalysts is that when the operating conditions are such as to permit complete elimination of the acetylene, a proportion of ethylene is also hydrogenated and converted to ethane. In addition, these single metal catalysts generally have relatively low stabilities due to the formation of a large amounts of oligomers formed, often referred to as green oil, which gradually cover the catalyst surface under operating conditions, thereby requiring frequent regeneration of the catalyst by some controlled oxidation process. A further disadvantage is that such catalyst may be quickly deactivated if used to hydrogenate acetylene in feed streams that contain relatively high amounts of acetylene, that is up to 10 or even 20 mass %.

Several other documents also address improving the performance of esp. Pd-based supported catalysts in hydrogenation of alkynes like acetylene. For example U.S. Pat. No. 5,648,576 discloses a process for selective hydrogenation in the gas phase of acetylene compounds containing 2 or 3 carbon atoms to the corresponding ethylene compounds in presence of hydrogen over a supported catalyst that have been surface modified with Pd and another metal from group IB, such as Ag, and optionally an alkaline or alkaline earth metal. Selective hydrogenation of acetylene is typically carried out on a feed containing 98% ethylene and 2% acetylene at a space velocity of 3300 $h^{-1}$.

In U.S. Pat. No. 6,350,717B1 a catalyst comprising at least one Group 10 and at least one Group 11 metal in specific ratios on an alumina support is described, wherein the Group 10 metals are concentrated in a surface layer of the support. The catalyst were used in hydrogenating acetylene in a 1/99 mixture with ethylene.

WO03/106020 describes modification of a supported Pd—Ag catalyst with an iodide compound, to improve performance in hydrogenating acetylene in a mixed feed stream containing up to about 1.5 mass of acetylene.

U.S. Pat. No. 7,153,807B2 discloses supported Ni— or Pt catalyst further comprising at least two other elements selected from Groups 8-9 and Groups 11-12, which show better hydrogenation selectivity on feed streams comprising up to about 2 mass % of acetylene U.S. Pat. No. 4,906,800 discloses a process for selectively converting a feed stream containing acetylene, ethylene and hydrogen into gasoline range hydrocarbons, wherein acetylene is hydrogenated by contacting with a Pd—Pb/$CaCO_3$ catalyst that is made by a process including specific oxidizing/reducing pre-treatment steps. Such a catalyst would be suited for treating feed mixtures containing relatively high amounts of acetylene, like a pyrolysis effluent gas; exemplified by an experiment on a stream containing 2.6 mass % of acetylene.

EP0689872A1 discloses a catalyst comprising palladium, silver and a support material useful in a process for selective acetylene hydrogenation. Prior to use, the catalyst is contacted with a liquid reducing agent which inter alia may be boronhydride.

WO02/16032 discloses a process for selective acetylene hydrogenation using a catalyst comprising an inorganic support material, a palladium component, a silver component and a promoter component "$XYF_n$," wherein said promoter component is a fluorine-comprising compound further consisting of an alkaline metal element and a further element which inter alia may be boron.

There remains a need in industry of a catalyst system showing high activity and selectivity, and good stability in hydrogenating alkynes in mixed feeds, also in feeds containing relatively high amounts of alkynes.

SUMMARY

The object of the invention is therefore to provide such a selective catalytic hydrogenation process for hydrogenating alkynes in mixed feeds.

The objective is achieved according to the invention as defined in the claims, especially with a process for selectively hydrogenating an alkyne to the corresponding alkene comprising a step of contacting a gaseous feed comprising hydrogen and 0.1-20 mass % of alkyne with a catalyst comprising at least one Group 10 element on a boron-modified support.

DETAILED DESCRIPTION

In the context of the present invention, the term "element on a boron-modified support" is meant to describe that the element is deposited on a support that was modified with boron prior to the deposition of said element on the support. Accordingly, a "catalyst comprising at least one Group 10 element on a boron-modified support" as employed in the process of the present invention represents a catalyst which is characterized in that at least one Group 10 element is deposited on a boron-modified support.

Surprisingly, the process of present invention allows selective hydrogenation of an alkyne like acetylene in to an alkene, eg ethylene, with higher conversion, and the catalyst showing better stability than prior art processes using catalysts without a boron-modified support. The catalyst shows high activity, enabling relatively short contact times, i.e. high space velocities, also referred to as GHSV, which enables integration of the process with other known processes such as methane reforming or methane pyrolysis generally used for ethylene synthesis, with typically only very short contact times and thus high flow rates. It is a further advantage of the process of the present invention that the activity of the inventive catalyst is less sensitive to the presence of some carbon monoxide in the feed.

U.S. Pat. No. 6,037,301 also discloses a boron-containing catalyst; containing an amorphous alloy of a Group VIII metal and boron, and a porous carrier. Most catalysts prepared in this document are Ni based and have been used in the removal of trace quantities of acetylene (typically less than 2 mol %) from an ethylene stream at GHSV of 9000 h$^{-1}$. In one experiment a Pd—La—B/SiO$_2$ amorphous alloy catalyst was tested on the hydrogenation of 4-carboxyl-benzaldehyde impurities in 4-carboxyl-benzoic acid. This document does not disclose or suggest applying a Ni, Pd or Pt catalyst on a boron-modified support material for alkyne dehydrogenation.

In the process according to the present invention alkyne is understood to include unsaturated hydrocarbon compounds having triple bonds, especially acetylene and propyne—also named methylacetylene-, and unsaturated compounds having more than one double bond, alkadienes like propadiene or butadiene; preferably alkynes are unsaturated compounds having triple bonds. Most preferably the alkyne is acetylene and the corresponding alkene is ethylene, or propyne and propylene, respectively.

The gaseous feed used in the process according to the invention contains alkyne and hydrogen, and optionally other components like an alkene, especially ethylene, alkanes like methane or ethane, liquid hydrocarbons, carbon monoxide, carbon dioxide, nitrogen, water, or other inert gases. Preferably, the feed further comprises at least one compound selected from the group consisting of ethylene, methane, ethane, carbon monoxide, carbon dioxide, nitrogen, and water.

The amount of alkyne, e.g. acetylene, in the feed gas may be in the range of from 0.1 to 20 mass %. The process according to the invention can be used to remove small amounts of alkynes from a feed stream, typically up to about 1 or 2 mass %, but the process has the distinct advantage that also relatively high acetylene concentrations can be reacted. The amount of acetylene in the feed gas is thus preferably at least 2 mass %, more preferably at least 4, 6, 8 or 10 mass %. Preferably, the feed gas contains at most about 18 mass % of acetylene, and more preferably at most about 16 or 14 mass % (based on the total mass of the feed). In a preferred way of operating the process according to the invention, the feed has been obtained by thermal pyrolysis of a hydrocarbon like methane.

The gaseous feed used in the process according to the invention contains hydrogen and alkyne, which may be present in widely varying amounts, for example in a molar ratio of from 0.5 to 10. It is an advantage that the process can be operated with high hydrogen concentrations without negatively affecting selectivity. Preferably, the feed contains more hydrogen than is stoichiometrically required for completing the hydrogenation reaction, that is the molar ratio of hydrogen to alkyne is preferably at least 1.0, 1.1 or 1.2, and at most 8, 6, 5, 4, or 3.

The inventors surprisingly found that the catalyst applied in the process according to the invention shows said advantageous performance if a suitable support if first modified with a boron compound, and then with the Group 10 metal. Preferably, the support is surface modified with boron, more preferably predominantly the surface of the support is modified. Most preferably, boron oxide, $B_2O_3$, is present on the surface of the support before Ni, Pd or Pt is added. Without wishing to be bound to any theory, the inventors assume that the presence of $B_2O_3$ (and active metal) on the surface of the support not only allows hydrogenation to occur in a short time, but also prevents deep hydrogenation a side reaction, e.g. hydrogenation of ethylene to ethane.

In the supported catalyst boron is preferably present in the range from about 0.1 to about 5 mass %, more preferably from 0.3 to 3 mass %. The mass ratio of the Group 10 metal component in the catalyst to boron ranges preferably from 10/3 to 1/6, more preferably from 1/1 to 1/5. Again without wishing to be bound to any theory, the inventors believe that an excess of B in the catalyst composition results in isolating at least some of the active metal centres from each other, and thus minimizing the risk of oligomerization or polymerisation reactions.

The content of a Group 10 element —Ni, Pd or Pt— in the catalyst preferably ranges from about 0.001 to about 2 mass %. A certain minimum content is needed to reach a desired level of catalyst activity, but a high content may increase the chance of active site agglomeration, and reduce efficiency of the catalyst. Therefore, the catalyst contains preferably at least 0.01, 0.03, 0.05, or 0.1 mass %, and at most 1, 0.8, or 0.5 mass % of Group 10 metals (based on total mass of the supported catalyst, excluding diluent). Preferably, the catalyst contains at least palladium as the active metal.

The catalyst in the process according to the invention may further contain other components, and can be represented by a generalized formula $M_1$-$M_2$-$M_3$-B/support catalyst, wherein the active component $M_1$ is at least one element selected from the group consisting of Ni, Pd and Pt, and B is boron, and $M_2$ and $M_3$ are optional elements. $M_2$ is a redox metal element with certain basic properties, which behaves as a promoter and is selected from the group consisting of Cu, Co, Cr, Pt, Ru, Au, Ag or a mixture thereof. The presence of these additional metals in the catalyst is found to improve the dispersion of active catalyst components and reduce the risk of agglomeration of the active sites, and to prevent side-reactions. Preferably the amount of $M_2$ present in the catalyst is 0-1 mass %, preferably 0.01-0.5 mass %.

The catalyst $M_1$-$M_2$-$M_3$-B/support in the process according to the invention may further contain component $M_3$, at least one element selected from the group consisting of alkali and alkaline earth metals. Preferably, $M_3$ is sodium or potassium. The presence of these additional metals in the catalyst is found to further improve performance. Preferably the amount of $M_3$ present in the catalyst is 0-1 mass %, preferably 0.01-0.5 mass %.

The catalyst used in the process according to the present invention comprises a carrier or support material of suitable particle size and geometry. Suitable supports include those materials having good stability at the reaction conditions to be applied in the method of invention, and are known to a person skilled in the art of catalysis. Preferably, the support material is at least one member selected from the group consisting of $SiO_2$, $ZrO_2$, $Al_2O_3$ and $TiO_2$, and mixtures thereof. $TiO_2$ is a specifically preferred support due to its basic character. The amount of support material present in the catalyst used in the method according to the present invention may vary within a broad range; a suitable range is from 40 to 99.87 mass % (based on total mass of catalyst). Preferably the support forms 50 to 95 mass % of the total catalyst composition. Preferably, particle size of the support (and supported catalyst) is from about 45 to 60 mesh.

In the process according to the invention the catalyst preferably is mixed with an inert solid binder or diluent, which is preferably selected from the group consisting of $SiO_2$, $ZrO_2$, $Al_2O_3$ and $TiO_2$ or mixtures thereof. This is particularly advantageous in case the process is performed in a fixed bed reactor on a feed that comprises more than 2 mass % of alkyne to increase selectivity by suppressing hydrogenation of alkenes to alkanes. The rationale may be that the diluent improves transfer or dissipation of exothermic reaction heat. In a preferred way of operating the process according to the invention, the diluent to catalyst ratio is from 2 to 250, more preferably 5-200, or 25-175 (on mass basis). In a preferred embodiment, the diluent is different from the support applied in the catalyst; for example in case the catalyst contains the preferred support $TiO_2$ the diluent may be $SiO_2$ (silica or quartz).

The process according to the invention can be performed over a wide temperature range, for example from 30 to 500° C. Preferably, the process is performed at a temperature of at least about 120° C., or 150, 200, 250 or even 275° C., but below 450, 400, 350 or even below 325° C. Higher temperatures generally increase conversion, but also favour side reactions like green oil formation. The process can be performed isothermally, or non-isothermally.

The process according to the invention can be performed over a wide pressure range, for example from about atmospheric conditions to 3 MPa. The process according to the invention may be carried out in different type of reactors, like a fixed bed reactor, which can be made from glass, quartz, ceramic and metallic material; as is known in the art. Fixed bed reactors typically have tubular structure, with inner diameter of about 4-50 mm, preferably 4-25 mm.

The contact time in the step of contacting the feed mixture comprising acetylene and hydrogen with a catalyst according to the process of the invention may vary widely, but is preferably about from 0.3 to 0.0005 s, more preferably from 0.001 to 0.0036 s. These very short contact times are in the same range of several other reactions. This is thus another advantage of the process according to the invention, enabling it to be integrated with other processes such as methane reforming for example. In the process according to the invention, because the GHSV is high, in the range 10,000 $h^{-1}$ to 7,000,000 $h^{-1}$, preferably about 1,000,000 to 4,000,000 $h^{-1}$, more preferably about 1,800,000 to 3,600,000 $h^{-1}$, a relatively small reactor size can be applied, which in turn leads to a reduction in the capital costs of the equipment.

The invention further relates to a method of preparing a catalyst $M_1$-B/support as defined in the above, comprising the steps of (a) modifying the support with boron, and (b) depositing at least one element $M_1$ selected from the group consisting of Ni, Pd and Pt on the boron-containing support.

Preferably, the step of (a) modifying the support with boron is done by (a1) treating a support with an aqueous solution of a boron compound; (a2) drying the treated support; and (a3) calcining the dried support to form boron oxides at the surface. Suitable boron compounds for step (a) are those that result in boron oxide formation in step (a3), which are known to a skilled person, such as boric acid ($H_3BO_3$). Drying, removing water, can be done at suitable conditions as known to skilled man, preferably at about 75-125° C. The temperature in step (a3) for calcining the dried support can vary widely, but is preferably about 200-400° C., more preferably 225-275° C.

Preferably, depositing at least one element $M_1$ selected from the group consisting of Ni, Pd and Pt on the boron-containing support in step (b) of the method according to the invention is done by (b1) impregnating the calcined support with an aqueous solution of $M_1$, and (b2) drying the impregnated support. The skilled man knows how to select suitable organic or inorganic salts, like acetates, nitrates or chlorides. Other methods like chemical vapour deposition or electrochemical methods can alternatively be applied.

The method of the invention can further comprise steps (c) and (d) of adding components $M_2$ and $M_3$ respectively, to make a composition represented by $M_1$-$M_2$-$M_3$-B/support as defined above, by techniques known to a skilled person, preferably by impregnation with aqueous solutions.

The method according to the invention to prepare the catalyst encompasses all variations and preferred compositions for the catalyst as discussed above. The method preferably further comprises a step (e) of mixing the impregnated support with a solid diluent, which diluent can be the same or different from the support. In a preferred way of preparing the catalyst according to the invention, the diluent is different from the support.

Preferably, the method according to the invention further comprises a step (f) of contacting the impregnated support with a reducing agent. Suitable conditions for this reduction step are about 200-400° C., preferably 225-275° C., using hydrogen or other suitable reducing agents during about 1-3 hours, preferably about 2 h.

In a preferred embodiment, the catalyst for use in the hydrogenation process of the invention is prepared by firstly treating the surface of a $TiO_2$ support with boric acid, drying off water at 120° C. followed by a calcination at 250° C. of the treated support to form boron oxide, then impregnating the B-modified support with palladium nitrate dissolved in an excess volume of water, followed by drying at 120° C. and reducing to a particle size of 40/60 mesh, mixing the catalyst with silica as inert diluent, and finally reducing the catalyst system with hydrogen for 2 hours at a temperature of about 250° C.

In one embodiment, the present invention relates to the process for selectively hydrogenating an alkyne to the corresponding alkene comprising a step of contacting a gaseous feed comprising hydrogen and 0.1 to 20 mass % of alkyne with a catalyst prepared by the method as described herein.

The invention will now be further illustrated with the following non-limiting experiments.

EXAMPLE 1

A $TiO_2$ support in the form of a gel was prepared by mixing an amount of $TiO_2$ with water to form a gel or a dense suspension as known to a person skilled in the art, and then impregnated with a boric acid ($H_3BO_3$) solution at 80° C. during 8 hours, followed by drying at 120° C. and calcining at about 250° C. to form $B_2O_3$. The solid material obtained was then impregnated with a 1% aqueous palladium nitrate solution at 80° C. The impregnated support was dried at about 120° C. during 12 hours to remove water, and crushed and sieved to obtain a particle size of 40-60 mesh. The thus obtained catalyst contained 0.5 mass % of Pd and 1 mass % of B. Upon loading to a fixed bed glass reactor having an internal diameter of 10 mm, 0.2 g of the catalyst particles were mixed with 10.5 g of $SiO_2$ having particle size in the same range as the catalyst. The catalyst system was then reduced by passing hydrogen for about 2 hours at a temperature of about 350° C.

Hydrogenation of acetylene was carried out by feeding an initial gas mixture of 9.8 mol % $C_2H_2$, 9.5 mol % $N_2$ and 80.7 mol % $H_2$ to the reactor at a flow rate of 1720 ml/min and at atmospheric pressure. Subsequently the effect of CO addition and air treatment was tested. Composition of gas streams was measured with gas chromatography, and reported in mol %. Space velocity during these experiments was about 540,000 $h^{-1}$ (calculated as gas flow rate in ml/h divided by amount of catalyst in ml; assuming catalyst density of about 1). Results are summarized in Table 1.

COMPARATIVE EXAMPLE 2

Analogously to Example 1 experiments were performed under the same conditions, but with a 0.5% Pd/$TiO_2$ catalyst made without the boron impregnation step.

Results summarized in Table 1 demonstrate lower conversion and stability for this non-boron containing catalyst.

TABLE 1

| Time (min) | Temp. (° C.) | Conversion (%) | Selectivity (%) $C_2H_4$ | $C_2H_6$ | Green oil | $C_2H_4$ yield (%) |
|---|---|---|---|---|---|---|
| Example 1 | | | | | | |
| 40 | 290 | 98.6 | 64.4 | 7.1 | 28.7 | 63.4 |
| 85 | 298 | 94.6 | 75.9 | 3.2 | 20.8 | 71.8 |
| 100 | 298 | 93.8 | 76.2 | 3.3 | 20.5 | 71.4 |
| Comparative example 2 | | | | | | |
| 30 | 270 | 61.0 | 86.5 | — | 13.5 | 52.7 |
| 60 | 270 | 49.0 | 84.5 | — | 15.5 | 41.4 |

EXAMPLE 3

Analogously to Example 1 experiments were done, but with a different quantity of the catalyst in the reactor, i.e. 0.057 g diluted with 10.4 g of quartz; at feed flow rate of 1800 ml/min; resulting in a space velocity of about 1,900,000 $h^{-1}$.

The results shown in Table 2 show good conversion, selectivity and catalyst stability.

EXAMPLE 4

Analogously to Examples 1 and 3 experiments were done, but with 0.03 g of 0.5% Pd-1% B/$TiO_2$ catalyst diluted with 10.4 g of quartz; at feed flow rate of 1800 ml/min; resulting in a space velocity of about 3,600,000 $h^{-1}$. Results presented in Table 2 show that still high conversion is obtained at this short contact time, maintaining selectivity and stability. Treatment with air after 1560 hours can at least partly regenerate catalyst activity.

TABLE 2

| Time (min) | Temp. (° C.) | Conversion (%) | Selectivity (%) $C_2H_4$ | $C_2H_6$ | Green oil | $C_2H_4$ yield (%) | $C_2H_2$ in product (%) |
|---|---|---|---|---|---|---|---|
| Example 3 | | | | | | | |
| 10 | 290 | 90.0 | 80.8 | 3.3 | 15.6 | 72.7 | 1.0 |
| 70 | 290 | 84.5 | 80.7 | 3.9 | 11.3 | 71.7 | 1.1 |
| 130 | 300 | 81.0 | 84.2 | 4.5 | 11.2 | 68.2 | 1.4 |
| 1560 | 302 | 79.1 | 89.7 | 3.3 | 7.0 | 70.8 | 2.2 |
| Example 4 | | | | | | | |
| 30 | 284 | 90.4 | 82.1 | 3.5 | 14.4 | 74.2 | 1.0 |
| 180 | 290 | 83.0 | 85.7 | 3.4 | 10.8 | 71.1 | 1.8 |
| 225 | 290 | 79.9 | 85.2 | 2.8 | 11.9 | 68.0 | 1.9 |
| 1560 | 298 | 69.0 | 82.1 | 5.6 | 12.3 | 56.6 | 3.2 |
| After treatment with air during 30 min at 300° C. | | | | | | | |
| 10 | 290 | 75.2 | 83.4 | 5.8 | 10.7 | 62.7 | 2.8 |

COMPARATIVE EXAMPLE 5

Applying the same conditions as above indicated, experiments were carried out, but using 0.035 g of a commercially available Pd—Ag/$Al_2O_3$ catalyst diluted with 10.4 g of quartz; at feed flow rate of 1800 ml/min. Results are given in Table 3.

These examples demonstrate higher acetylene conversion and better stability of a Pd—B/support catalyst according to the invention than that of a non B-modified supported Pd catalyst, or a commercial Pd—Ag/$Al_2O_3$ catalyst.

TABLE 3

| Time (min) | Temp. (° C.) | Conversion (%) | Selectivity (%) $C_2H_4$ | $C_2H_6$ | Green oil | $C_2H_4$ yield (%) | $C_2H_2$ in product (%) |
|---|---|---|---|---|---|---|---|
| 10 | 290 | 59.1 | 84.7 | 3.3 | 12.0 | 50.0 | 4.2 |
| 80 | 292 | 46.3 | 81.4 | 5.8 | 12.7 | 37.6 | 5.5 |

What is claimed is:

1. Process for selectively hydrogenating an alkyne to the corresponding alkene comprising a step of contacting a gaseous feed comprising hydrogen and 0.1 to 20 mass % of alkyne with a catalyst comprising at least one Group 10 element deposited on a boron-modified support, wherein $B_2O_3$ is present on the surface of the support when the at least one Group 10 element is deposited.

2. Process according to claim 1, wherein at least Pd is deposited on a boron-modified support.

3. Process according to claim 1, wherein the catalyst is represented by generalized formula $M_1$-$M_2$-$M_3$-B/support wherein said catalyst contains 0.03 to 1 mass % of at least one element $M_1$ selected from the group consisting of Ni, Pd and Pt; 0-1 mass % of at least one element $M_2$ selected from the group consisting of Cu, Co, Cr, Pt, Ru, Au and Ag; 0-1 mass % of at least one element $M_3$ selected from the group consisting of alkali and alkaline earth metals; and 0.1 to 5 mass % of boron.

4. Process according to claim 1, wherein the support is selected from the group consisting of $SiO_2$, $ZrO_2$, $Al_2O_3$ and $TiO_2$ or mixtures thereof.

5. Process according to claim 1, wherein the catalyst further contains a solid diluent selected from the group consisting of $SiO_2$, $ZrO_2$, $Al_2O_3$ and $TiO_2$ or mixtures thereof, with diluent to support mass ratio of from 2 to 250, and wherein the diluent is different from the support.

6. Process according to claim 1, wherein the alkyne in the feed is acetylene and the corresponding alkene is ethylene.

7. Process according to claim 1, wherein the feed further comprises at least one compound selected from the group consisting of ethylene, methane, ethane, carbon monoxide, carbon dioxide, nitrogen, and water.

8. Process according to claim 1, wherein the gaseous feed stream contains from 4 to 16 mass % of acetylene.

9. Process according to claim 1, wherein the molar ratio of hydrogen to alkyne in the feed is from 1.1 to 5.

10. Process according to claim 1, wherein the hydrogenation is performed at a temperature of 120-450° C. and a pressure of from atmospheric to 3 MPa.

11. Process according to claim 1, wherein the process is carried out at a space velocity of 1,000,000 to 4,000,000 $h^{-1}$.

* * * * *